(12) United States Patent
Kimura

(10) Patent No.: US 6,430,422 B1
(45) Date of Patent: Aug. 6, 2002

(54) INTRAORAL JIG FOR OPTICAL MEASUREMENT

(75) Inventor: Eiichi Kimura, Osaka (JP)

(73) Assignee: Kurabo Industries Ltd., Okayama (JP)

( * ) Notice: Subject to any disclaimer, the term of this patent is extended or adjusted under 35 U.S.C. 154(b) by 48 days.

(21) Appl. No.: 09/620,379

(22) Filed: Jul. 20, 2000

(30) Foreign Application Priority Data

Jul. 23, 1999 (JP) .......................................... 11-209922

(51) Int. Cl.$^7$ ................................................ A61B 5/00
(52) U.S. Cl. ........................ 600/310; 600/322; 600/344
(58) Field of Search .............................. 600/309–310, 600/322–324, 316, 344, 364–365, 473–478; 356/39–42

(56) References Cited

U.S. PATENT DOCUMENTS

| | | | | |
|---|---|---|---|---|
| 4,510,941 A | * | 4/1985 | Semrow et al. | 600/484 |
| 4,852,549 A | * | 8/1989 | Mori | 607/92 |
| 5,078,153 A | * | 1/1992 | Nordlander et al. | 600/590 |
| 5,392,777 A | * | 2/1995 | Swedlow et al. | 600/322 |
| 5,553,615 A | * | 9/1996 | Carim et al. | 600/324 |
| 5,601,079 A | * | 2/1997 | Wong et al. | 600/322 |
| 5,772,587 A | * | 6/1998 | Gratton et al. | 600/310 |
| 6,018,674 A | * | 1/2000 | Aronow | 600/322 |
| 6,243,601 B1 | * | 6/2001 | Wist | 600/473 |
| 6,253,097 B1 | * | 6/2001 | Aronow et al. | 600/310 |

* cited by examiner

Primary Examiner—Eric F. Winakur
Assistant Examiner—Matthew Kremer
(74) Attorney, Agent, or Firm—Rader, Fishman & Grauer, PLLC

(57) ABSTRACT

A jig body of resin is formed with a concave part engaging with an upper backside of teeth and another concave part engaging with a lower backside of teeth, and includes a portion coming into contact with an oral cavity part. An optical fiber bundle for measurement is embedded in the jig body, and a forward-end-surface of the optical fiber bundle is exposed on the portion of the jig body coming into contact with the oral cavity part and flush with the portion. A heater and a temperature sensor for keeping the temperature of the jig body constant as well as a pressure sensor for detecting a pressure for holding the jig body between the upper and lower teeth of a measured person are further embedded in the jig body.

10 Claims, 6 Drawing Sheets

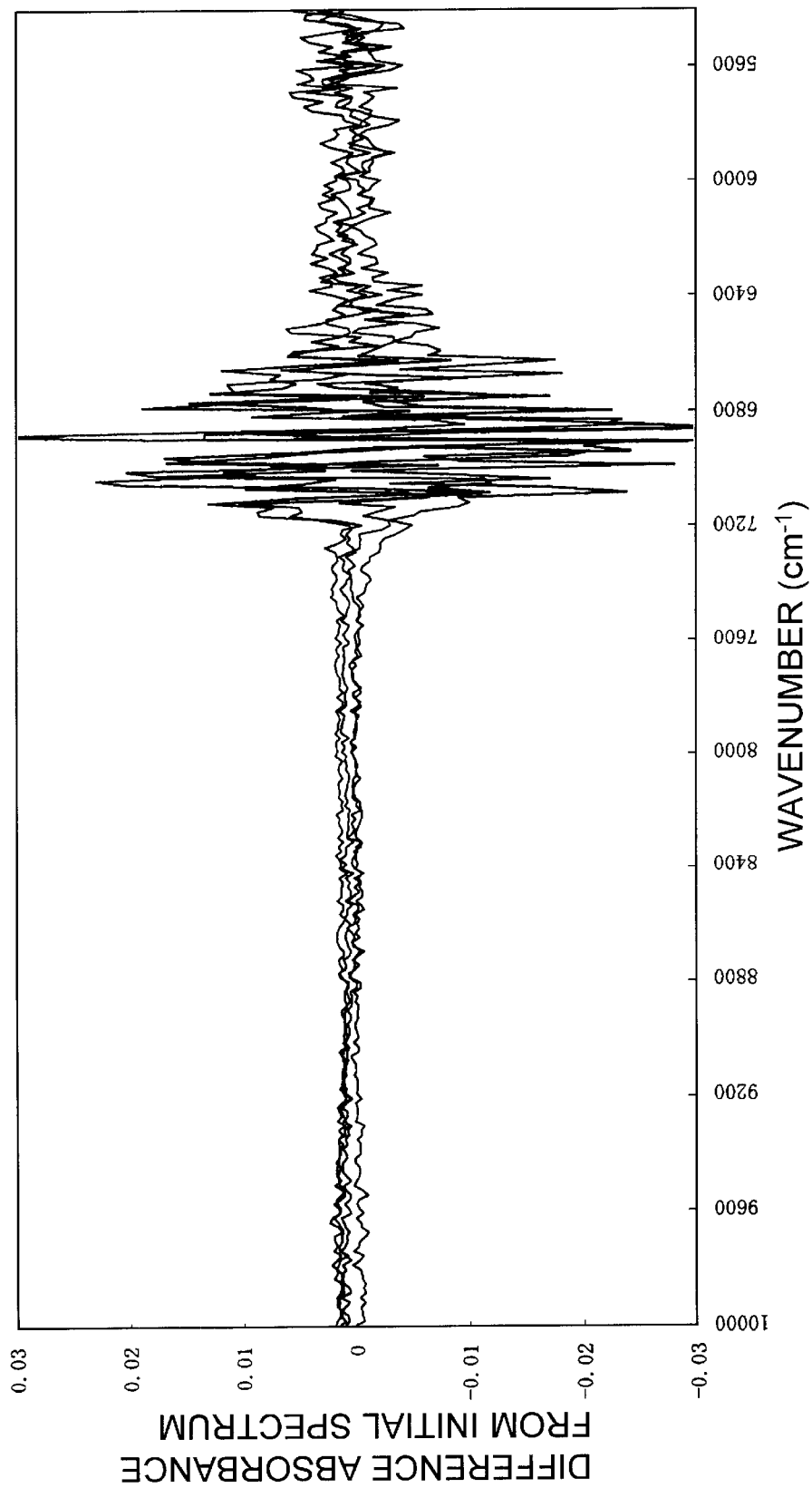

TIME CHANGE WITH UNCONTROLLED TEMPERATURE (PRIOR ART)

INTRAORAL JIG FOR OPTICAL MEASUREMENT

BACKGROUND OF THE INVENTION

1. Field of the Invention

The present invention relates to a jig for non-invasively measuring a physical quantity of a vital tissue by bringing a projecting/photoreceiving forward-end-surface into contact with an organism. This jig is used, for example, for irradiating a human body with light of a near-infrared region and measuring a physical quantity in the human body such as a glucose concentration in blood or oxygen saturation of blood by an output light from the human body through the light.

2. Description of the Prior Art

In the field of clinical testing, a non-invasive measuring method of irradiating an organism with light and measuring oxygen saturation in blood or a blood-sugar level from output light is attempted. The organism is a scatterer having an internal structure complicatedly varying with places, and hence an optical path length of light must be made constant in the organism, in order to measure a concentration of blood-sugar level and the like.

When bringing a measuring probe into contact with a vital tissue for applying light and measuring output light, influence is exerted by position reproducibility, the degree of contact, the surface temperature of a human body, the thickness of a corneum layer, a moisture content, and the like. In order to avoid such influence, intraoral measurement with a mouthpiece is proposed (refer to "Medical Electronics and Bioengineering", Vol. 35, special edition (April 1997), p. 512).

In this proposal, pulse waves, pulses and oxygen saturation are listed as objects measured with light. In measurement of these objects, however, absolute value measurement does not have to be made and hence necessity for noting the degree of adhesion between the mouthpiece and the oral cavity and the degree of contact between an optical light guide component such as an optical fiber member and the oral cavity is low and not sufficiently taken into consideration. Therefore, when measuring a physical quantity of such as a blood-sugar level requiring absolute value measurement, reproducibility is deteriorated. When a projecting/photoreceiving forward-end-surface projecting measuring light and receiving scattered light from an organism is inferiorly in contact with an intraoral surface, it comes to also receive light reflected by the intraoral surface leading to deterioration of an S-N (signal-to-noise) ratio. Contrary to this, when the contact between the projecting/photoreceiving forward-end-surface and the organism is too strong, congestion takes place.

The temperature of the mouthpiece coming into contact with the intraoral surface is also important. If a vital tissue is influenced by the temperature of the mouthpiece, the obtained absorption-spectrum disadvantageously changes.

SUMMARY OF THE INVENTION

An objective of the present invention is to provide a jig for intraorally measuring a physical quantity of a vital tissue with excellent reproducibility.

The present invention is directed to an intraoral jig for optical measurement comprising a jig body having a shape engaging with upper and lower backsides of teeth of a measured person and coming into contact with an oral cavity part, a projecting/photoreceiving part embedded in the jig body so that a projecting/photoreceiving forward-end-surface is flush with a portion coming into contact with the oral cavity part for projecting measuring light to the oral cavity part and receiving an output light from the oral cavity part through the measuring light on the forward-end-surface, a temperature control mechanism keeping a temperature of the jig body constant and a pressure sensor embedded in the jig body for detecting a pressure for holding the jig body between the upper and lower teeth of the measured person.

The output light from the oral cavity part and received by the projecting/photoreceiving part includes all light output from the oral cavity part such as transmitted light, scattered light and reflected light after projection of the light to a human body.

This jig body has the shape engaging with the upper and lower backsides of teeth of the measured person and coming into contact with the oral cavity part, and the projecting/photoreceiving part is embedded in the jig body so that the forward-end-surface thereof is flush with the portion of the jig body coming into contact with the oral cavity part, whereby contact between the forward-end-surface of the projecting/photoreceiving part and the internal surface of the oral cavity as well as position reproducibility are improved. Furthermore, influence by the temperature can be eliminated by keeping the temperature of the jig body constant with the temperature control mechanism, and influence by the pressure can also be eliminated by holding the jig between the upper and lower teeth of the measured person so that the pressure detected by the pressure sensor is constant.

The projecting/photoreceiving part includes a projecting part and a photoreceiving part. These parts can be arranged to be close to or separate from each other.

The projecting part can be a light-guide-path such as an optical fiber bundle guiding the measuring light from a light source. In this case, the degree of freedom in light source selection is increased, wavelength selection is easy, and it is also easy to obtain high luminous energy. It is also possible to arrange a spectroscope separating the light from the light source into its spectral components between the light source and the light-guide-path. Alternatively, the projecting part can be provided with a light emitting device such as an LED (light emitting diode) or an LD (laser diode) embedded therein.

The photoreceiving part can be a light wave path such as an optical fiber bundle guiding the received output light to a detector. In this case, the degree of freedom in detector selection is increased. It is also possible to arrange a spectroscope separating the output light into its spectral components between the light-guide-path and the detector. Alternatively, the photoreceiving part can be provided with a photoreceiving element such as a photodiode or a phototransistor embedded therein.

Light from near-infrared or infrared region is preferable as light for measuring a physical quantity of a vital tissue. The light source being used, generating light included in such a wavelength region, may include a continuous spectrum or discontinuous bright line spectra in this wavelength region. An LED or an LD for near-infrared or infrared emission can be employed as such a light source, in addition to a tungsten-halogen lamp.

The detector or the photoreceiving element is sensitive to a near-infrared or infrared region, and a Ge photodiode, an InGaAs photodiode, a PbS photoconductive element, a PbSe photoconductive element, an InAs photovoltaic element or a pyroelectric element can be employed as such an infrared detector.

If the temperature is around the body temperature of a human body when keeping the temperature of the jig body by the temperature control mechanism constant, influence by the temperature is preferably minimized. The foregoing and other objects, features, aspects and advantages of the present invention will become more apparent from the following detailed description of the present invention when taken in conjunction with the accompanying drawing.

BRIEF DESCRIPTION OF THE DRAWINGS

FIG. 2 is a waveform diagram showing a plurality of near-infrared absorption spectra measured with the jig according to the embodiment while keeping both the temperature and pressure constant as difference absorbance spectra;

DESCRIPTION OF THE PREFERRED EMBODIMENTS

Figure 1A:
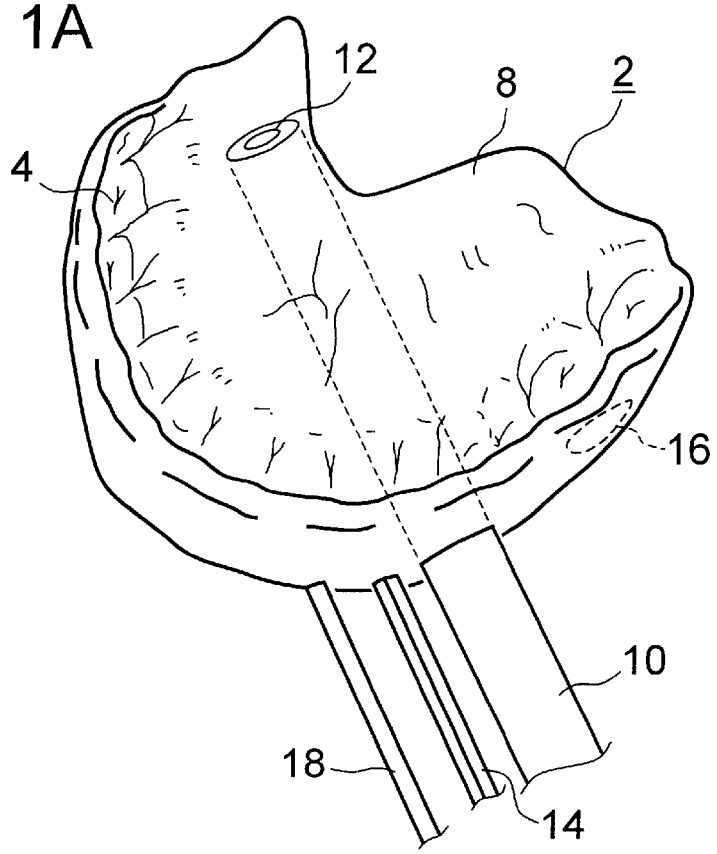
FIGS. 1A and 1B are perspective views showing a jig according to an embodiment of the present invention at different angles respectively.
Figure 1B:
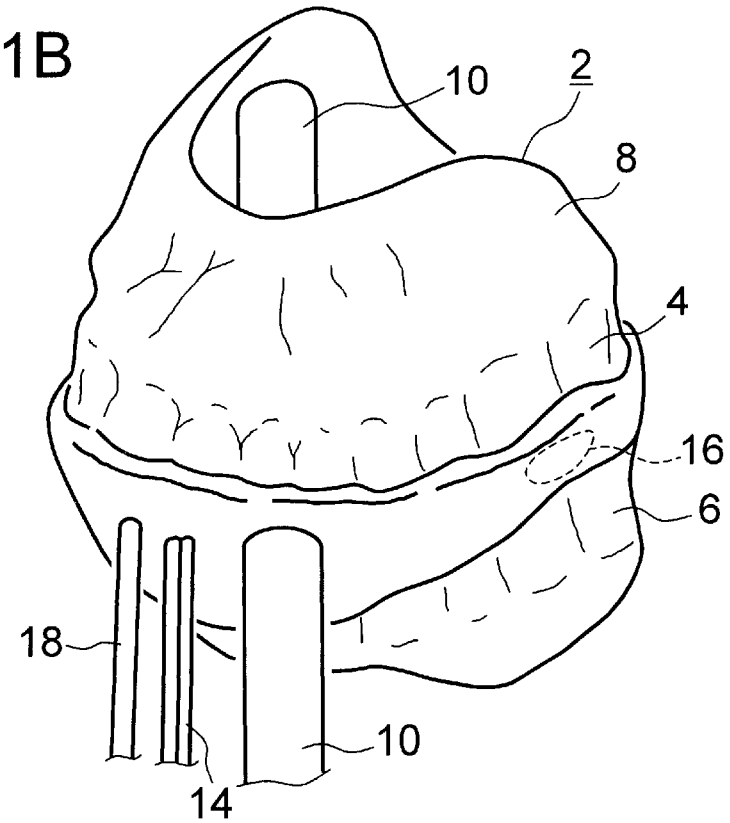

FIGS. 1A and 1B are perspective views showing a jig according to an embodiment of the present invention at different angles respectively.

A jig body 2 of resin, molded in response to the intraoral shape of each measured person, is formed with a concave part 4 engaging with an upper backside of teeth, and another concave part 6 engaging with a lower backside of teeth, and comprises a part 8 coming into contact with an oral cavity part. The part 8 coming into contact with the oral cavity part preferably comes into contact with the oral cavity part over a wide area, in order to avoid stress concentration to the oral cavity part. When putting the jig body 2 into a mouth and engaging upper and lower teeth in the concave parts 4 and 6 respectively, the part 8 comes into contact with the oral cavity part.

An optical fiber bundle 10 is embedded in the jig body 2 as a projecting/photoreceiving light-guide-path, in order to irradiate the oral cavity part with measuring light and receive the measuring light scattered in and output from the organism of the oral cavity part. A forward-end-surface 12 of the optical fiber bundle 10 is exposed on the part 8 of the jig body 2 coming into contact with the oral cavity part, and flush with this part 8. The measuring light is guided by the optical fiber bundle 10 from an external optical measuring apparatus, applied to the oral cavity part from the forward-end-surface 12 and scattered or reflected by the organism of the oral cavity part, to re-enter the forward-end-surface 12. The forward-end-surface 12, coming into contact with the oral cavity part along with the part 8, does not reflect the measuring light. The base end of the optical fiber bundle 10 is guided to the external optical measuring apparatus comprising a light source, a spectroscope and a photodetector, so that a light absorption spectrum in the near-infrared region can be measured.

A heater and a temperature sensor are embedded in the jig body 2 as a temperature control mechanism keeping the temperature of the jig body 2 constant. A cable 14 supplies power to the heater from an external power source and guides a temperature detection signal from the temperature sensor to an external control unit controlling the quantity of energization of the heater.

A pressure sensor 16 for detecting a pressure for holding the jig body 2 between the upper and lower teeth of the measured person is embedded in the jig body 2. The position for embedding the pressure sensor 16, not particularly restricted, is for example in the vicinity of the concave part 4 engaging with the upper back teeth of the measured person. Another cable 18 guides a detection signal from the pressure sensor 16 to an external display unit. The contact pressure between the part 8 and the oral cavity part can be rendered constant by adjusting the force for holding the jig between the upper and lower teeth of the measured person so that the pressure detected by the pressure sensor 16 is constant in each measurement, for rendering the contact pressure between the forward-end-surface 12 of the optical fiber bundle 10 and the oral cavity part constant in particular.

When intraorally measuring an intravital physical quantity such as a blood-sugar level with this jig, the heater and the temperature sensor keep the jig body 2 at a temperature of, for example, 37° C. around the body temperature of a human body, and the jig body 2 is put into the oral cavity of the measured person. The measured person engages the upper and lower teeth in the concave parts 4 and 6 respectively, holds the jig body 2 between the upper and lower teeth so that the pressure sensor 16 displays a prescribed pressure value, projects the measuring light from the optical fiber bundle 10 at the prescribed pressure value, and measures an absorption spectrum thereof.

FIG. 2 shows exemplary measurement with the jig according to this embodiment The temperature of the jig body 2 is kept at 37° C. and near-infrared absorption spectrum measurement is repeated five times while keeping the pressure for holding the jig between the upper and lower teeth of the measured person constant thereby obtaining and displaying difference in absorbance (difference absorbance) with respect to an initial spectrum. Turbulence of the spectra around 7000 $cm^{-1}$ results from influence by water.

Figure 3:
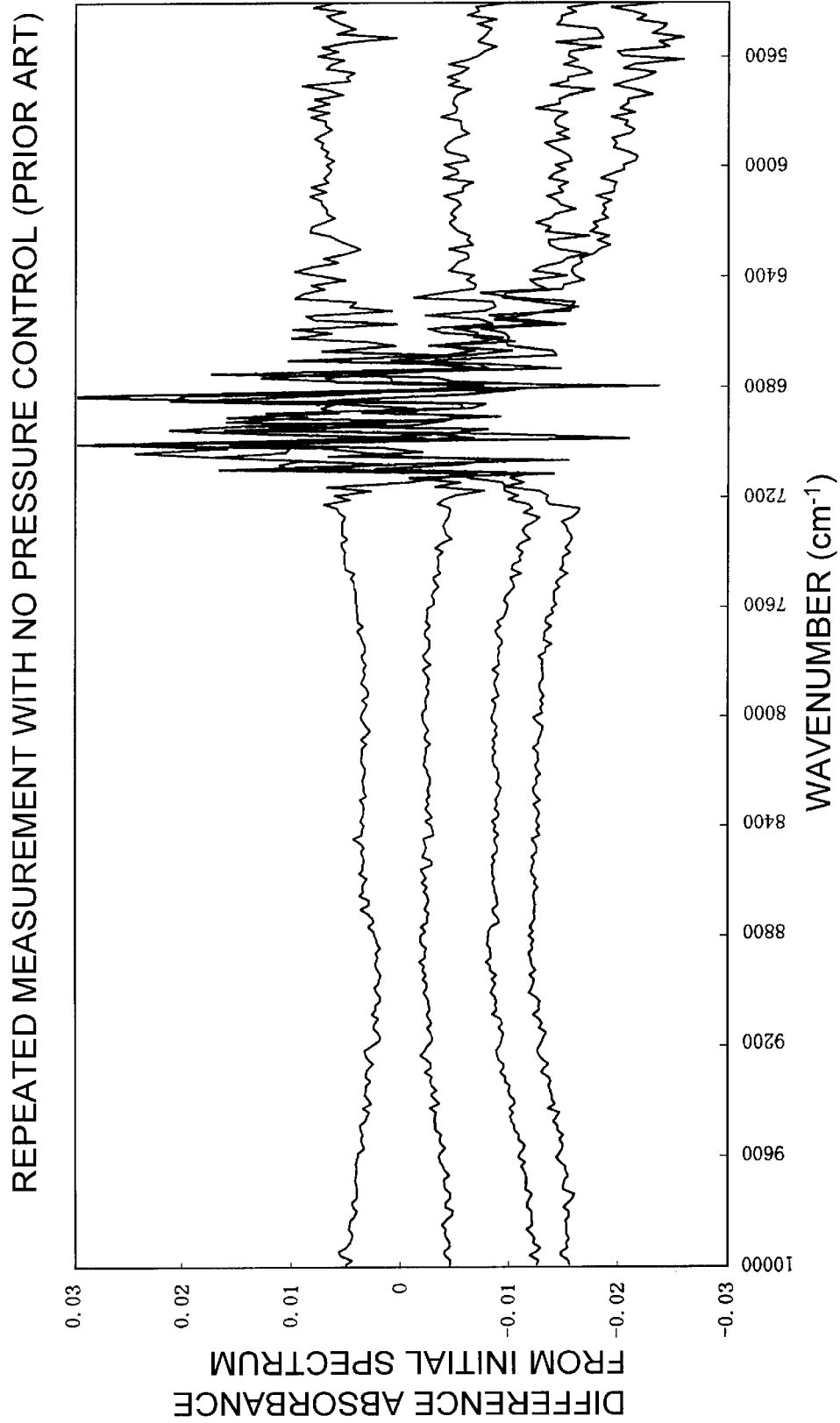
FIG. 3 is a waveform diagram showing a plurality of near-infrared absorption spectra measured with the jig according to the embodiment while keeping the temperature constant with no pressure control as difference absorbance spectra.

FIG. 3 shows results of difference absorbance obtained by performing spectrum measurement while holding the jig between the upper and lower teeth of the measured person under an arbitrary pressure with no pressure control.

Figure 4:
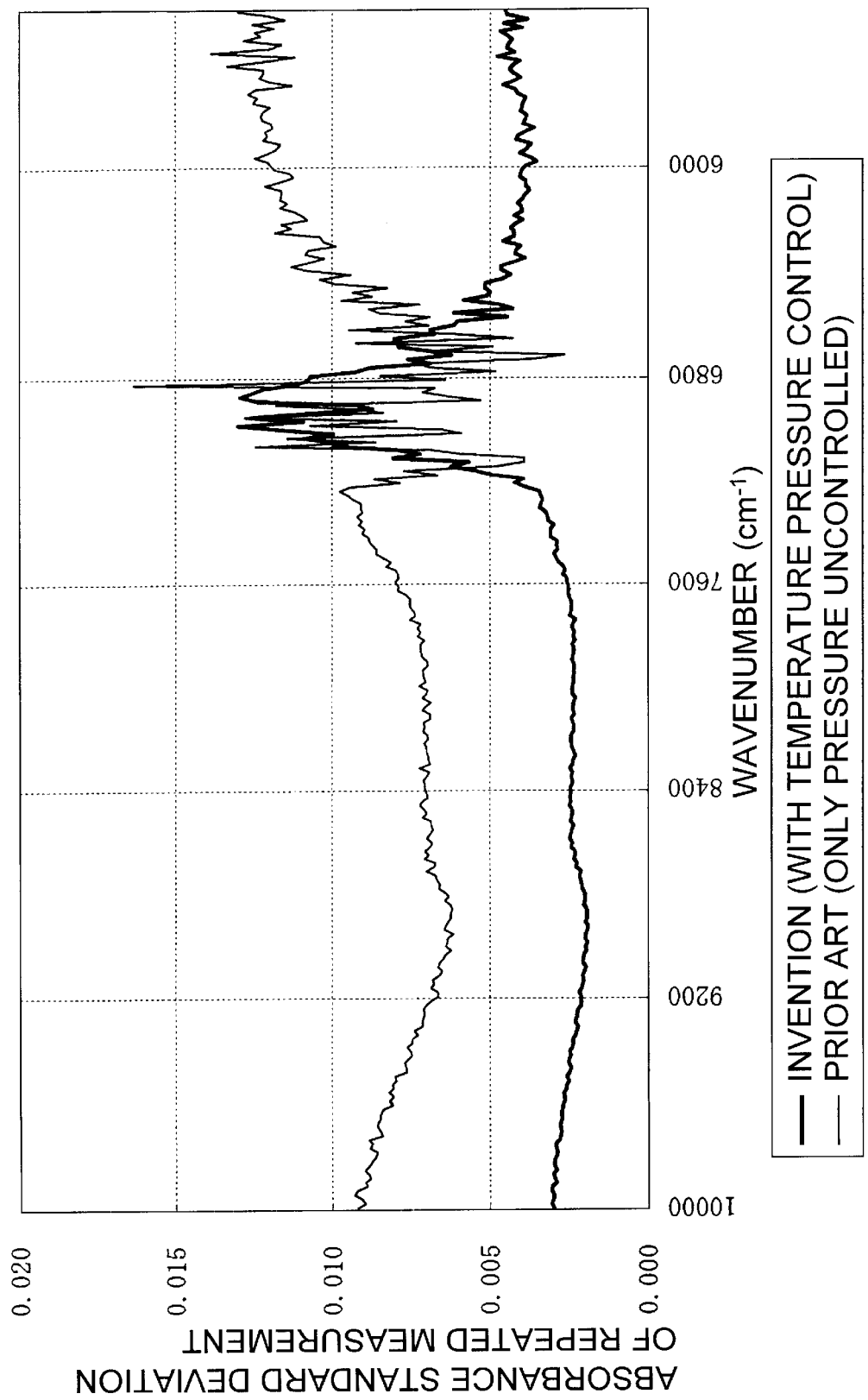
FIG. 4 is a waveform diagram showing absorbance standard deviation obtained from the results shown in FIGS. 2 and 3.

Comparing FIGS. 2 and 3 with each other, the spectra disperse every measurement when performing no pressure control. In order to clarify this, FIG. 4 shows absorbance standard deviation obtained from the results shown in FIGS. 2 and 3. The thick solid line shows the result of FIG. 2 measured while keeping the temperature and the pressure constant according to the present invention, and the thin solid line shows the result of FIG. 3 obtained by keeping the temperature constant with no pressure control. It is understood that reproducibility of the measurement result is improved by keeping the contact pressure between the forward-end-surface 12 of the optical fiber bundle 10 and the oral cavity part constant.

Figure 5:
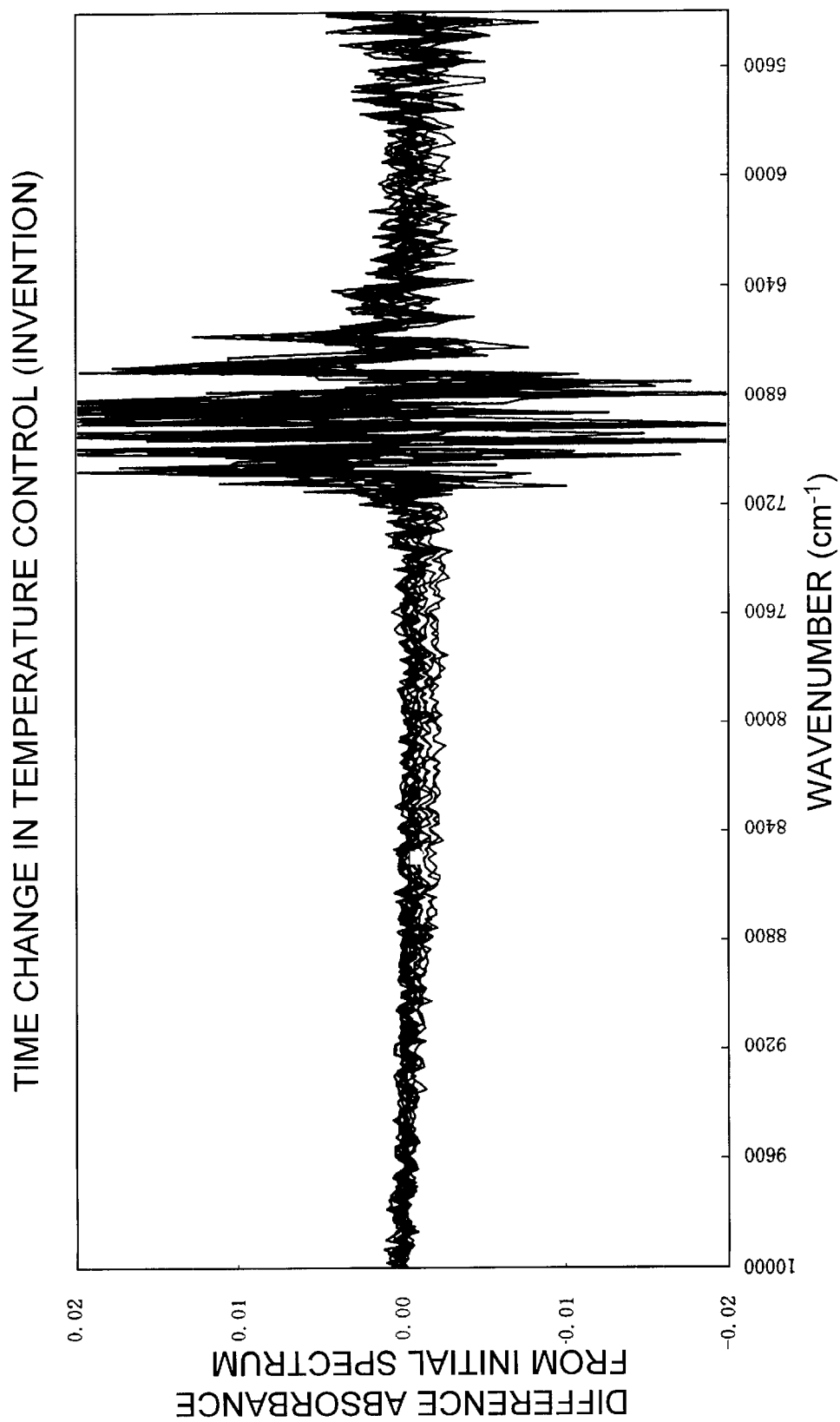
FIG. 5 is a waveform diagram showing difference absorbance spectra obtained by repeating measurement at regular time intervals with the jig according to the embodiment while keeping both the temperature and pressure constant.

An effect of temperature control shall now be described. FIG. 5 shows results obtained by repeating near-infrared absorption spectrum measurement on a regular basis for 14 times while keeping both temperature and pressure constant as difference absorbance from an initial spectrum similarly to FIG. 2.

Figure 6:
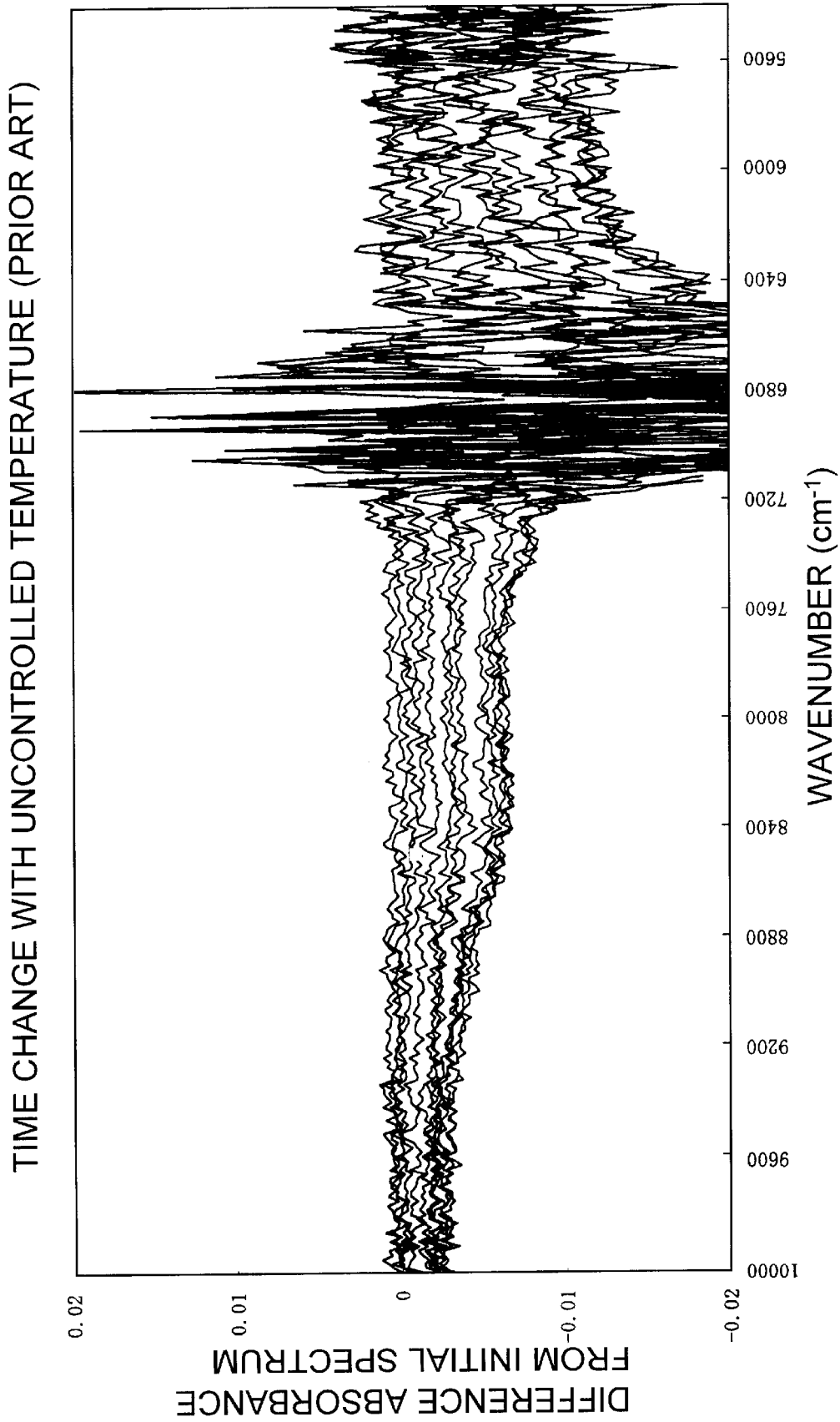
FIG. 6 is a waveform diagram showing difference absorbance spectra obtained by repeating measurement at regular time intervals with the jig according to the embodiment while keeping the pressure constant with no temperature control.

FIG. 6 shows results obtained by repeating measurement at regular time intervals while keeping the pressure constant without temperature-controlling the jig.

As understood through comparison of the results shown in FIGS. 5 and 6, fluctuation of an absorption spectrum caused by temperature change with time can be suppressed by keeping the temperature of the jig body according to the present invention.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. An intraoral jig for optical measurement, comprising:
   a jig body having a shape adapted for engaging with upper and lower backsides of teeth and coming into contact with an oral cavity part of a person to be measured, said jig body being prepared exclusively for said person;
   a projecting/photoreceiving part embedded in said jig body so that a surface of the projecting/photoreceiving part is flush with a portion coming into contact with said oral cavity part for projecting measuring light to said oral cavity part from said projecting/photoreceiving surface and receiving an output light from said oral cavity part through a measuring light portion on said projecting/photoreceiving surface;
   a temperature control mechanism keeping a temperature of said jig body constant or substantially constant; and
   a pressure sensor embedded in said jig body for detecting a pressure for holding said jig body between upper and lower teeth of said person, the pressure being held constant or substantially constant and the temperature control mechanism controls the temperature of the jig body constant or substantially constant while the projecting/photoreceiving part projects the measuring light and receives the output light.

2. The intraoral jig for optical measurement according to claim 1, wherein
   said projecting/photoreceiving part includes a light guide path guiding said measuring light from a light source as a projecting pat and a light guide path guiding received output light to a detector as a photoreceiving part.

3. The intraoral jig for optical measurement according to claim 1, wherein
   said projecting/photoreceiving part includes a light guide path guiding said measuring light from a light source as a projecting part and a photoreceiving element embedded in said projecting/photoreceiving surface as a photoreceiving part.

4. The intraoral jig for optical measurement according to claim 1, wherein
   said projecting/photoreceiving part includes a light emitting device embedded in said projecting/photoreceiving surface as a projecting part and a light guide path guiding received output light to a detector as a photoreceiving part.

5. The intraoral jig for optical measurement according to claim 1, wherein
   said projecting/photoreceiving part includes a light emitting device embedded in said projecting/photoreceiving surface as a projecting part and a photoreceiving element embedded in said projecting/photoreceiving surface as a photoreceiving part.

6. The intraoral jig for optical measurement according to claim 1, wherein
   said temperature kept constant is a temperature around a body temperature of a human body.

7. The intraoral jig for optical measurement according to claim 1, wherein the projecting/photoreceiving part is an optical fiber bundle.

8. The intraoral jig for optical measurement according to claim 1, at least one of the measuring light and the output light is near-infrared light.

9. The intraoral jig for optical measurement according to claim 1, wherein the oral cavity part is a palate of the mouth of the person.

10. The intraoral jig for optical measurement according to claim 1, wherein the temperature control mechanism includes a heater.

* * * * *